United States Patent
Fontana et al.

(10) Patent No.: US 9,000,205 B2
(45) Date of Patent: Apr. 7, 2015

(54) PROCESS FOR THE PREPARATION OF 2-CYANOPHENYLBORONIC ACID AND ESTERS THEREOF

(71) Applicant: F.I.S.—Fabbrica Italiana Sintetici S.p.A., Montecchio Maggiore, Vicenza (IT)

(72) Inventors: Francesco Fontana, Como (IT); Emiliano Rossi, Trento (IT); Christian De Filippo, Vicenza (IT)

(73) Assignee: F.I.S.—Fabbrica Italiana Sintetici S.p.A., Montecchio Maggiore-Vicenza (IT)

( * ) Notice: Subject to any disclaimer, the term of this patent is extended or adjusted under 35 U.S.C. 154(b) by 0 days.

(21) Appl. No.: 14/370,174

(22) PCT Filed: Jul. 24, 2013

(86) PCT No.: PCT/EP2013/065660
§ 371 (c)(1),
(2) Date: Jul. 1, 2014

(87) PCT Pub. No.: WO2014/023576
PCT Pub. Date: Feb. 13, 2014

(65) Prior Publication Data
US 2014/0357886 A1 Dec. 4, 2014

(30) Foreign Application Priority Data
Aug. 6, 2012 (IT) ............... MI2012A1390

(51) Int. Cl.
C07F 5/04 (2006.01)
C07D 295/155 (2006.01)
C07D 213/64 (2006.01)
C07F 7/02 (2006.01)
C07C 253/30 (2006.01)
C07F 5/02 (2006.01)

(52) U.S. Cl.
CPC .............. *C07F 5/04* (2013.01); *C07D 295/155* (2013.01); *C07D 213/64* (2013.01); *C07F 7/025* (2013.01); *C07C 253/30* (2013.01); *C07F 5/025* (2013.01); *C07F 5/027* (2013.01)

(58) Field of Classification Search
CPC ........................................................ C07F 5/04
USPC ........................................................ 558/288
See application file for complete search history.

(56) References Cited

U.S. PATENT DOCUMENTS

2009/0184289 A1   7/2009   Nakamura

FOREIGN PATENT DOCUMENTS

EP   1582523 A1   10/2005
EP   1772450 A1   4/2007

OTHER PUBLICATIONS

International Search Report issued in PCT Application No. PCT/EP2013/065660, Nov. 28, 2013.
Charles McElhinny Jr. et al: "A Practical, Laboratory-Scale Synthesis of Perampanel", Synthesis, vol. 44, No. 01, (Jan. 1, 2012), pp. 57-62, XP055054279, ISSN: 0039-7881, 001: 10.1055/s-0031-1289587 Schemes 1-4.
R. Dabrowski et al: "Synthesis and mesogenic properties of three- and four-ring compounds with a fluoroisothiocyanatobiphenyl moiety", Liquid Crystals, vol. 37. No. 12, (Dec. 10, 2010), pp. 1529-1537, XP055054269. ISSN: 0267-8292. DOI: 10.1080/02678292. 2010.521983 Scheme 1, p. 1530, p. 1530. col. 1. paragraph 2.
Urawa Y et al: "Investigations into the Suzuki-Miyaura coupling aiming at multikilogram synthesis of E2040 using (o-cyanophenyl) boronic esters", Journal of Organometallic Chemistry, Elsevier-Sequoia S.A. Lausanne, CH, vol. 653. No. 1-2, (Jul. 1, 2002), pp. 269-278, XP004361529, ISSN: 0022-328X. DOI: 10.1016/S0022-328X(02)01175-0, p. 270. Schemes 1 and 3, p. 271; table 1, p. 270, paragraph 2.1, Reaction (3), p. 271.
Fabian M. Piller et al: "Convenient Preparation of Polyfunctional Aryl Magnesium Reagents by a Direct Magnesium Insertion in the Presence of LiCl", Angewandte Chemie International Edition, vol. 47, No. 36, (Aug. 25, 2008), pp. 6802-6806, XP055007491, ISSN: 1433-7851, DOI: 10.1002/anie.200801968 p. 6803; table 1; compound 2a, Experimental section; p. 6805, p. 6802, col. 2, Last paragraph, col. 1, p. 6805.
Krasovskiy Arkady et al: "Transition-metal-free homocoupling of organomagnesium compounds", Angewandte Chemie. International Edition, Wiley VCH Verlag, Weinheim, vo 1. 45, No. 30, (Jan. 1, 2006), pp. 5010-5014, XP002495939, ISSN: 1433-7851, DOI: 10.1002/ANIE.200600772, p. 5011; table 1; compound 3f Experimental section; p. 5014.

(Continued)

*Primary Examiner* — Samantha Shterengarts
(74) *Attorney, Agent, or Firm* — Lucas & Mercanti, LLP

(57) ABSTRACT

The present invention relates to a process for the synthesis of 2-cyanophenylboronic acid and the esters and salts thereof of formula (II), which are intermediates of the synthesis of active pharmaceutical ingredients such as Perampanel or E2040. formula (II): (II).

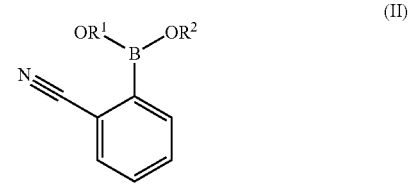

21 Claims, 1 Drawing Sheet

(56) References Cited

OTHER PUBLICATIONS

Malgorzata Myslinska et al: "Practical and efficient applications of novel dioxaborolanes and dioxaborinanes in the synthesis of corresponding boronates and their use in the palladium-catalyzed cross coupling reactions", Tetrahedron Letters, Elsevier, Amsterdam, NL, vol. 53, No. 24, (Mar. 14, 2012), pp. 2937-2941, XP028424181, ISSN: 0040-4039, DOI: 10.1016/J.TETLET.2012.03.048, [retrieved on Mar. 29, 2012], the whole document.

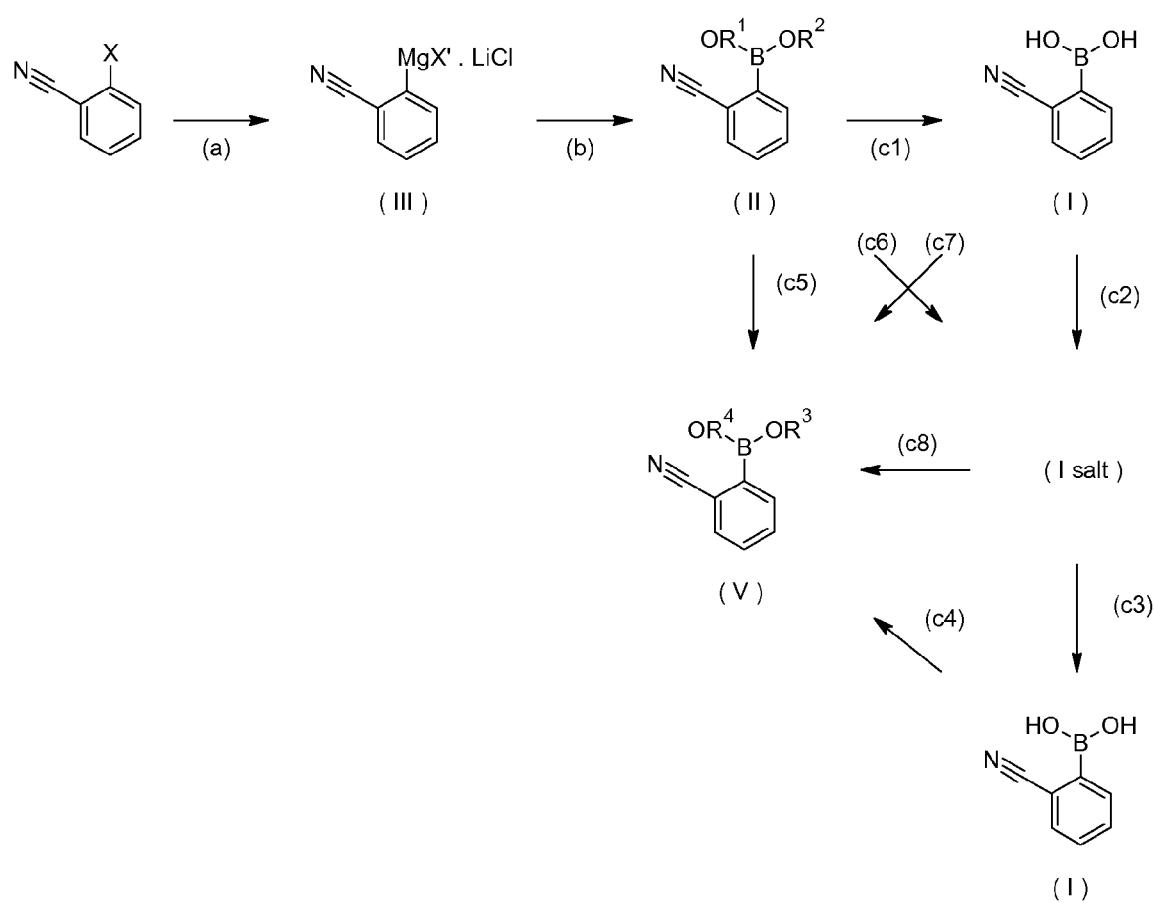

US 9,000,205 B2

PROCESS FOR THE PREPARATION OF 2-CYANOPHENYLBORONIC ACID AND ESTERS THEREOF

CROSS-REFERENCE TO RELATED APPLICATIONS

This application is a 371 of PCT/EP2013/065660 filed Jul. 24, 2013, which claims the benefit of Italian Patent Application No. MI2012A001390, filed Aug. 6, 2012, the contents of each of which are incorporated herein by reference.

TECHNICAL FIELD OF THE INVENTION

The object of the present invention is a process for the synthesis of 2-cyanophenylboronic acid and the esters and salts thereof, which are intermediates of the synthesis of active pharmaceutical ingredients such as Perampanel or E2040.

BACKGROUND OF THE INVENTION

Perampanel is a pharmaceutical active ingredient, currently in clinical phase 3, used in the treatment of Parkinson's disease, epilepsy and multiple sclerosis.

Perampanel, having the following chemical formula

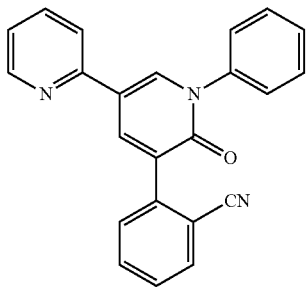 [SMILES: N#Cc1ccccc1-c1cc(-c2ccccn2)cn(-c2ccccc2)c1=O]

is also known as E 2007, ER 155055-90 and 3-(2-Cyanophenyl)-1-phenyl-5-(2-pyridyl)-1,2-dihydropyridin-2-one.

There are various known synthesis routes of this molecule, such as those reported in patent publications EP1300396, EP1465626, EP1772450, EP1764361 and EP1970370.

Many of the synthesis routes of this active ingredient reported in the prior art employ the key intermediate 2-(1,3,2-dioxaborinane-2-yl)benzonitrile having the following chemical formula:

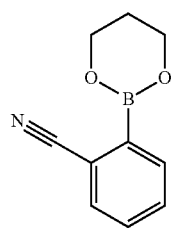 [SMILES: N#Cc1ccccc1B1OCCCO1]

or employ the synthetic precursor thereof called 2-cyanophenylboronic acid of formula (I):

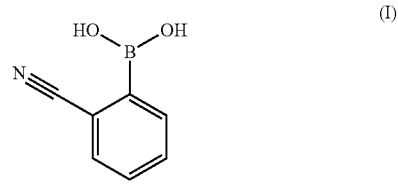 [SMILES: N#Cc1ccccc1B(O)O]

The 2-(1,3,2-dioxaborinane-2-yl)benzonitrile is indeed quantitatively prepared by simple esterification with 1,3-propanediol of the 2-cyanophenylboronic acid of formula (I), as well reported in the prior art.

There are several synthesis routes of the 2-cyanophenylboronic acid of formula (I). From an industrial viewpoint, the most interesting process to date for the preparation of this compound is the process described in patent publication US2009/0184289 wherein, starting from Benzonitrile, n-butyllithium and 2,2,6,6-tetramethylpiperidine at −78° C. are employed to generate the ortho-anion which, by reacting with triisopropoxyborane and subsequent acid hydrolysis of the diisopropyl ester of the 2-cyanophenylboronic acid obtained, gives the desired product. The highest molar yield reported is 71%. This process appears to be an improvement with respect to the process described in the Organic Letters of 2001, Vol. 3, no. 10, pages 1435-1437. This process however, has obvious disadvantages, such as the need to operate in cryogenic conditions (T=−78° C.) using special equipment, while obtaining the product in relatively low molar yield. The product also contains an impurity typical of that synthetic process.

The Journal of Organometallic Chemistry (2002), 653 (1-2), 269-278 reports the synthesis of the pharmaceutical active ingredient called E2040 by means of the compound of formula (I) or an ester thereof, of which there is mention and description of and the preparation of the key intermediate 2-(1,3,2-dioxaborinane-2-yl)benzonitrile by means of esterification with 1,3-propanediol by the compound of formula (I). The preparation of the compound of the formula (I) is carried out by ortho-bromobenzonitrile with a halogen/lithium exchange and attachment of the anion onto the trimethoxyborane, followed by hydrolysis of the dimethyl ester. A yield of about 50% is reported, which for industrial purposes is of little interest.

SUMMARY OF THE INVENTION

The problem addressed by the present invention is thus that of making available an improved process for the preparation of 2-cyanophenylboronic acid of formula (I) and the esters thereof:

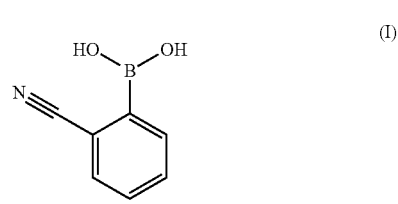 [SMILES: N#Cc1ccccc1B(O)O]

that makes it possible to at least partially overcome the above-reported drawbacks with reference to the prior art.

This problem is resolved by a synthesis process of the 2-cyanophenylboronic acid of formula (I) or of an ester thereof as outlined in the accompanying claims, the definitions of which form an integral part of the present description.

Further characteristics and advantages of the process according to the invention will become apparent from the below-reported description of preferred embodiments, given by way of a non-limiting example.

BRIEF DESCRIPTION OF THE DRAWINGS

FIG. 1 Shows a summary and explanatory synthesis pathway of the synthesis steps and variants of the process of the present invention.

DETAILED DESCRIPTION OF THE INVENTION

The present invention relates to a process for the preparation of an ester of 2-cyanophenylboronic acid of formula (II):

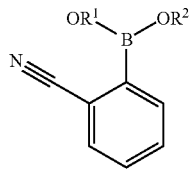

wherein R1 and R2 are independently linear or branched C1-C6 alkyl groups or are combined to form a cycle comprising between 1 and 6 possibly substituted carbon atoms comprising the following steps:

(a) conversion of a 2-halogenbenzonitrile of formula (IV):

(IV)

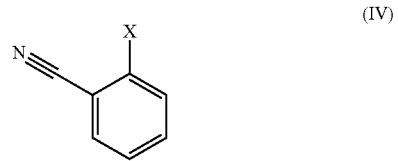

wherein X is selected from chlorine, bromine and iodine, in a 2-cyanophenyl magnesium halide lithium chloride complex of formula (III):

(III)

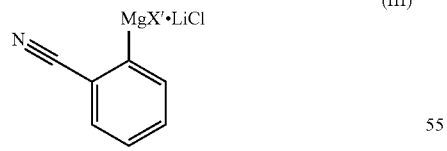

wherein X' is selected from chlorine, bromine and iodine;
(b) conversion of the compound obtained in step (a) to give the compound of formula (II).

Step (a) according to the process of the present invention is carried out by means of a Lithium chloride complex Grignard reagent. It is preferably performed by means of a Grignard reagent selected from Isopropylmagnesium chloride lithium chloride complex and t-Butylmagnesium chloride lithium chloride complex.

Indeed, it has been found that in order to successfully carry out step (a) starting from the substrate of formula (IV), it is essential to use a lithium chloride complex Grignard reagent since the possible use of a normal Grignard reagent does not lead to even small amounts of the corresponding boronic ester. A normal Grignard reagent indeed allows the preparation of the corresponding Grignard, however since it is not a lithium chloride complex, it does not react like one to form the boronic ester of formula (II). From here, the process of the present invention passes through the Grignard reagent intermediaries of formula (III) which are lithium chloride complexes which are the only ones to provide the compound of formula (II).

An obvious advantage of the process according to the present invention is that the formation of the Grignard reagent (step (a)) is performed between 0 and 5° C., and since step (b) is carried out starting from this temperature, both the use of cryogenic conditions and equipment typical of the other processes of the prior art, and the need to perform long thermal ramps on industrial-scale production are avoided. It being neither necessary nor practical to isolate the intermediate Lithium chloride complex Grignard reagent, it is thus possible to use a one-pot reaction for the entire process, even by always operating at the same temperature, for example, preferably between 0° C. and 5° C.

Alternatively, step (b) can also be fully or partially performed at a temperature between 20 and 25° C.

If the 2-halogenbenzonitrile of formula (IV) has a halogen group X that differs from the halogen of the lithium chloride complex Grignard reagent employed for the reaction, the corresponding product of formula (III) will have a group X' that could be the same starting 2-halogenbenzonitrile or X' could be the halogen of the Grignard reagent used or a mixture of compounds could be obtained with the two different halogens. In all cases, the reaction products are to be construed as being part of the present invention.

It has also been surprisingly found that the molar yield of the above-described process comprising steps (a) and (b) to give the compound of formula (II) is 80-85% and thus much greater than the processes of the prior art.

The process of the present invention can comprise a further (c1) step of conversion of the compound of formula (II) obtained in step (b) in the 2-cyanophenylboronic acid of formula (I):

(I)

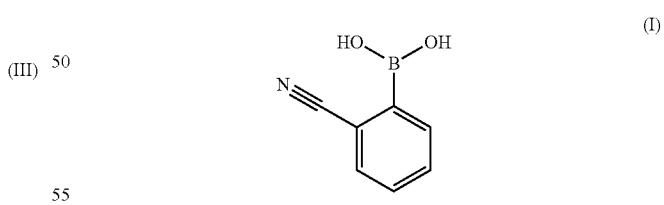

This step (c1) can be carried out with water or acidic water and is quantitative whereby the yield of the entire process to obtain the 2-cyanophenylboronic acid of formula (I) is 80-85%.

Some conditions for performing step (c1), for example by means of acid hydrolysis of the ester, are also described in US2009/0184289.

The 2-cyanophenylboronic acid of formula (I) obtained from step (c1) can be further converted by means of the further step (c2) in an organic or inorganic salt, in the 2-cyanophenylboronic acid of formula (I).

This organic salt can present as counter-ion a primary, secondary or tertiary aliphatic or aromatic amine. Examples of organic counter-ions are triethylamine, dimethylamine, methylamine, benzylamine, aniline, etc. The inorganic salts of the 2-cyanophenylboronic acid of formula (I) comprise as counter-ions ammonium and the cations of alkaline elements (for example sodium, lithium, potassium, caesium, etc.) and alkaline-earth elements (for example calcium, magnesium, strontium, barium, etc.). Preferred are the sodium, potassium and magnesium salts of the 2-cyanophenylboronic acid of formula (I).

It is evident that if the counter-ion cation is monovalent, the salt will consist of two cations while if it is divalent, the salt will have a single counter-ion atom, i.e. it will have stoichiometry (1:1).

The process of the present invention can comprise the further direct conversion step (c6) of the compound obtained in step (b) in an organic or inorganic salt of the 2-cyanophenylboronic acid of formula (I).

This is achieved for example by placing in contact the organic solution containing the compound of formula (II) with an aqueous solution at pH>9 containing soda or potash for example. There is thus obtained the corresponding salt in aqueous phase.

The process of the present invention can comprise a further conversion step (c3) of the compound obtained in step (c2) or (c6) in the 2-cyanophenylboronic acid of formula (I).

This step can be realised for example by acidifying an aqueous solution containing the salt obtained in step (c2) or (C6) and, possibly, extracting the product in a suitable organic solvent or by isolating the product by means of precipitation.

The process of the present invention can comprise a further conversion step (c4) of the compound obtained in step (c3) in an ester of the 2-cyanophenylboronic acid formula (V):

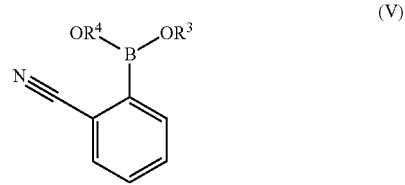

(V)

wherein R3 and R4 are independently linear or branched C1-C6 alkyl groups or are combined to form a cycle containing 1 to 6 possibly substituted carbon atoms.

This esterification step, like step (c7), can be performed employing conditions of the prior art such as those described in the Journal of Organometallic Chemistry (2002), 653(1-2), 269-278.

The process of the present invention can further and alternatively comprise a further conversion (c8) step of the compound obtained in step (c2) or (c6) in an ester of the 2-cyanophenylboronic acid of formula (V):

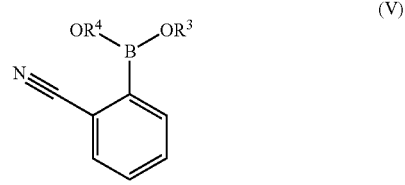

(V)

wherein R3 and R4 are independently linear or branched C1-C6 alkyl groups or are combined to form a cycle containing 1 to 6 possibly substituted carbon atoms.

Although in the formula (II) and in formula (V) the R substituent groups have different names, i.e. R1 and R2 versus R3 and R4, it should be noted that the meaning of the compound of the ester of the 2-cyanophenylboronic acid of formula (II) is the same as that of formula (V).

In one preferred embodiment, the process of the present invention allows the preparation by means of steps (a) and (b) or by means of steps (c4) or (c8) of the 2-(1,3,2-dioxaborinane-2-yl)benzonitrile compound of the following formula:

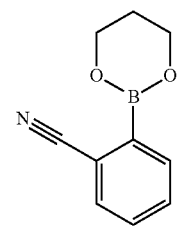 [SMILES: N#Cc1ccccc1B1OCCCO1]

In one preferred embodiment, the process of the present invention, in all the variants thereof, employs in step (a) the 2-bromobenzonitrile, i.e. the compound of formula (IV) wherein X is bromine.

The process according to the present invention, in all the variants or alternatives thereof, provides for step (b) to be carried out by means of a compound of formula X1-B(OR1)(OR2) where X1 is selected from halogen and OR wherein R is a linear or branched C1-C6 alkyl group and where R1 and R2 are independently linear or branched C1-C6 alkyl groups or are combined to form a cycle containing between 1 and 6 possibly substituted carbon atoms.

Preferably, step (b) is carried out with a compound wherein X1 is selected from chlorine, OMe and OiPr and R1 and R2 are selected from Methyl, isopropyl or form a cycle having 3 carbon atoms not substituted.

Even more preferred as reagents for achieving step (b) are trimethyl borate or triisopropylborate.

The process of the present invention provides for step (c2) to be carried out by extraction of an organic solution of the compound of formula (I) with an aqueous solution at pH greater than 9 comprising an organic or inorganic base, wherein the organic or inorganic salt of the 2-cyanophenylboronic acid of formula (I) thus generated is then to be found.

Preferably, the pH of the aqueous solution is between 10 and 14.

Step (b) indeed generally terminates with the obtaining of the compound of formula (II) in an organic solution consisting of one or more organic solvents, such as for example Toluene or mixtures of Toluene and THF. This solution can be treated according to step (c6) or according to step (c2) (by means of hydrolysis according to step (c1)) with a basic aqueous solution (at pH greater than 9) into which the product of formula (I) is transferred in the form of salt. The organic phase having been exhausted, it is thus eliminated. The aqueous phase can then be washed with some organic solvent. The aqueous phase containing the compound of formula (I) in the form of salt can thus be re-acidified, according to step (c3), thus obtaining the compound of formula (I) in the form of acid that can be separated from the aqueous phase by precipitation or by means of extraction with an organic solvent. This solvent can preferably be the same solvent from which the product was extracted by means of the basic aqueous solution.

Alternatively, ethyl acetate, or better isopropyl acetate, can be conveniently used. These steps (C2) and (C3) allow the purity of the compound of formula (I) to be increased from typical values for the crude product obtained from step (c1) from 82-83% to more than 96-98% (purity measured with HPLC (A/A %).

It is important to highlight that, if the 2-cyanophenylboronic acid of formula (I) is not isolated and preparation of the compound of formula (V) takes place without first carrying out step (c2) and possibly step (c3), for example by directly performing step (c7), the product of formula (V) does not crystallize and tends to remain as, often sticky, oil. This is probably due to the presence of the impurities that are on the other hand removed with the organic phase exhausted by means of the basic extraction. In order to obtain the compound of formula (I) with a degree of sufficient purity to allow isolation of the compound of formula (V) in solid form, the purification step (c2) by means of basic extraction of the product is thus essential.

By including steps (c2) and (c3) of purification by means of basic treatment, i.e. by obtaining the salt of the compound of formula (I) and subsequent re-acidification and extraction in organic solvent, a product of formula (V) is obtained that is easily filterable and certainly has a greater degree of purity. In addition, the process of the present invention allows 2-cyanophenylboronic acid of formula (I) with a level of purity (HPLC (A/A %)) greater than 98% to be obtained.

The expert of the sector knows that, generally speaking, the arylboronic acids, especially those electron poor, are subjected to proto deboration reaction when they are treated under basic conditions. Evidences of this general knowledge are reported in "Boronic Acids" "preparation, Applications, Organic Synthesis and Medicine" edited by Dennis G. Hall for Wiled-VCH Verlag GmbH (2005), at pag. 14. Thus, it is surprising that, vice-versa, preparing the organic or inorganic salt of the 2-cyanophenylboronic acid of formula (I), according to the steps (c1) and (c2), or, alternatively according to the step (c6), thus treating 2-cyanophenylboronic acid or an ester thereof at pH greater than 9, and preferably higher than 10, allow the preparation of a purer product so that it can be isolated as solid.

The process according to the present invention provides for steps (a) and/or (b) and/or (c2) to be carried out in an organic solvent selected from Toluene, Tetrahydrofuran (THF), methyl-tetrahydrofuran or mixtures thereof. Preferably, steps (a) and (b) are carried out in Toluene or mixtures of Toluene and THF.

It is preferable to one-pot synthesize the ester of formula (V) since the 2-cyanophenylboronic acid of formula (I), according to what is reported in the Journal of Organometallic Chemistry (2002), 653 (1-2), 269-278, could be a relatively unstable substance and not conveniently usable for productions on industrial scale.

To this end, as a variant, once there has been obtained, with the process of the invention, the compound of formula (II), for example wherein R1 and R2 are both methyl or isopropyl, the trans-esterification step (c5) can be performed, using for such purposes for example the teachings of the Organic Letters of 2001, Vol. 3, no. 10, pages 1435-1437.

Step (a) according to the present invention thus allows the preparation of the 2-Cyanophenyl magnesium halide lithium chloride complex of formula (II):

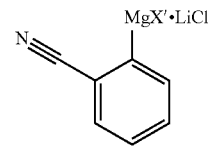

(II)

wherein X' is selected from chlorine, bromine and iodine, by means of the 2-halogenbenzonitrile conversion of formula (III):

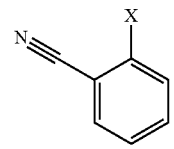

(III)

wherein X is selected from chlorine, bromine and iodine.

The process of the present invention allows the preparation of 2-cyanophenylboronic acid of formula (I) or a salt thereof:

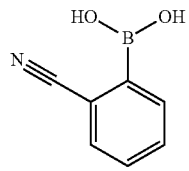

(I)

by means of a process comprising the extraction of an organic solution of the compound of formula (I) with an aqueous solution at pH greater than 9 comprising an organic or inorganic base wherein the organic or inorganic salt of the 2-cyanophenylboronic acid of formula (I) thus generated is then to be found.

The process of the present invention can be employ as intermediate an organic or inorganic salt of the 2-cyanophenylboronic acid of formula (I):

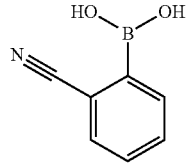

(I)

preferably selected from sodium salt, potassium salt and magnesium salt.

The halide of 2-cyanophenyl magnesium halide lithium chloride complex of formula (II) and the organic or inorganic salt of the cyanophenylboronic acid of formula (I) are thus used for the preparation of 2-cyanophenylboronic acid of formula (I) or of an ester thereof of formula (II) or (V) or for the preparation of Perampanel or of E2040.

The compound of formula (I) obtained with the process according to the present invention can be possibly isolated according to known organic synthesis techniques.

According to a preferred embodiment, the step a) of the process of the invention, is preferably carried out within a range of temperature comprised between −25° C. and −15° C. and more preferable, between −22° C. and −18° C., being about −20° C. the best temperature. It has been indeed surprisingly discovered that performing the step a) in a temperature range comprised between −25° C. and −15° C. the molar yield increase dramatically. When step a) is performed at this temperature, as in Example 2, the molar yield of the final isolated 2-(1,3,2-dioxaborinane-2-yl)benzonitrile increase until 73%, versus a 44.8% obtained performing the step a) at 0-5° C. (see example 1). In general terms, operating step a) −25° C./−15° C. instead at 0° C./5° C. the isolated molar yield of 2-(1,3,2-dioxaborinane-2-yl)benzonitrile increases from 40-45% to 73-75%. Although to perform the reaction of step a) at 0-5° C. is already an improvement either in terms of molar yield or purity in respect of performing this reaction at 20-25° C., performing this reaction at −25° C./−15° C., and preferably at −22° C./−18° C. or at about −20° C., provides exceptional results.

Operating the step a) in the preferred range of −25° C./−15° C. allows a dramatic increasing of molar yield (the reaction of step a) is thus almost quantitative (complete conversion with very few impurities) and the molar yield of the final 2-(1,3,2-dioxaborinane-2-yl)benzonitrile reaches 73%) and is also observed an increase of the purity of the final product (from 99.7% of Experiment 1 to 99.9% of Experiment 2). This is mainly due to the fact that performing step a) at −25° C./−15° C. the formation of the dimeric impurity having the following structure:

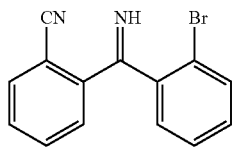 [SMILES: N#Cc1ccccc1C(=N)c1ccccc1Br]

is completely avoided, even operating at higher concentration (which should favourite the formation of this impurity). This impurity is in fact particularly critical for this process since once it is formed, it is not eliminated during the synthesis and is subjected to the same chemical transformations as the other intermediates, thus generating the final impurity having the following structure:

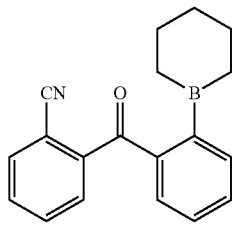 [SMILES: N#Cc1ccccc1C(=O)c1ccccc1B1CCCCC1]

The removal of the above impurity of the 2-(1,3,2-dioxaborinane-2-yl)benzonitrile is indeed particularly difficult and decreases the level of purity of the 2-(1,3,2-dioxaborinane-2-yl)benzonitrile itself, as well as of the final pharmaceutical substance Perampanel or E2040.

Performing the step a) at −25° C./−15° C. and preferably at −22° C./−18° C., the reaction is much more clean, i.e. there are much less impurities, than performing the reaction at 0-5° C. or, worse at 20-25° C. This also contributes to the achieving of higher molar yields.

Although the increase of the chemical purity could appear modest, this not the case, vice-versa it is actually a valuable improvement since, as known by the person of the sector, passing from 99.7% to 99.9% of chemical purity is difficult and requires typically a large amount of experimental work.

According to a preferred embodiment, the step a) of the process of the invention is carried out within a range of temperature comprised between −25° C. and −15° C., more preferable at −22° C. and −18° C., and the process comprises the conversion step (c1) of the compound obtained in step (b) in the 2-cyanophenylboronic acid of formula (I):

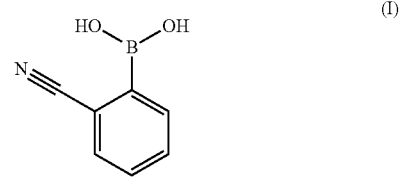 [SMILES: N#Cc1ccccc1B(O)O]

and comprises the conversion step (c2) of the compound obtained in step (c1) in an organic or inorganic salt of the 2-cyanophenylboronic acid of formula (I), or, alternatively to the steps (c1) and (c2), the process comprises the direct conversion step (c6) of the compound obtained in step (b) in an organic or inorganic salt of the 2-cyanophenylboronic acid of formula (I) which is then converted in the ester of 2-cyanophenylboronic acid of formula (V):

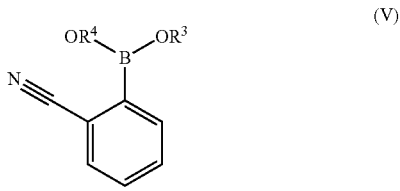

wherein R3 and R4 are independently C1-C6 linear or branched alkyl groups or are joined to form a cycle containing between 1 and 6 possibly substituted carbon atoms, through the step (c8) or the steps (c3) and (c4). This preferred embodiment allows the preparation of esters of 2-cyanophenylboronic acid of formula (V) which can be isolated as solid and having high chemical purity. The high chemical purity of the product is indeed reached thank to the temperature range of −25° C. and −15° C. of step a) and thank to the purification carried out through the preparation of an organic or inorganic salt of the 2-cyanophenylboronic acid of formula (I) which allows the isolation of the product as a solid, instead as an oil, thus increasing significantly the chemical purity.

According to a preferred embodiment of the invention, a process for the preparation of the 2-(1,3,2-dioxaborinane-2-yl)benzonitrile is summarized in the synthesis pathway included in the examples 1 and 2 and comprises the sequences of steps (a), (b), (c1), (c2), (c3) and (c4) as well as the intermediates as shown in such synthesis pathway.

EXPERIMENTAL SECTION

Example 1

Synthesis of 2-(1,3,2-dioxaborinane-2-yl)benzonitrile

Synthesis Pathway

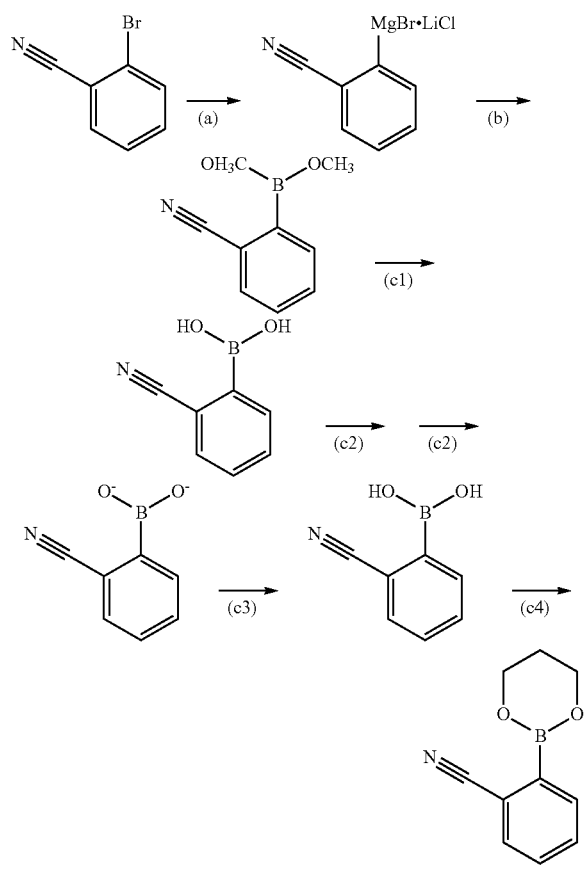

Into a previously dried and inertised flask under nitrogen flow, fitted with a thermometer, reflux and a dropping funnel, are loaded 50.0 g (1.0 equiv.) of 2-bromobenzonitrile and 250 ml (5 V) of anhydrous Toluene. It is cooled at 0-5° C. and there are added, in 0.5 hours and maintaining the T at 0-5° C., 269.0 g (1.35 equiv.) of Isopropylmagnesium chloride/lithium chloride complex 1.3 M (about 20% wt/wt) in THF. It is stirred at T 0-5° C. and stirred for 1.5 hours. The conversion in checked in HPLC. If the reaction is complete there are added in 0.25 hours at 0-5° C., 57.0 g=61.3 ml (2 equiv.) of trimethylborate (d=0.932 g/ml). It is stirred at 0-5° C. for 0.25 hours and then allowed to warm to 20-25° C. and stirred for 0.25 hour. The conversion is checked in HPLC. If the reaction is complete, it is cooled to 0-5° C. and there is added at 0-10° C. a solution of hydrochloric acid 0.1 M prepared by mixing 5 ml of hydrochloric acid 32% (10.17 M) and 495 ml (9.9 V) of purified water. It is left under agitation 0.5 h at 20-25° C. and then the pH, which must be less than 5, is checked. If the pH is not less than 5, sufficient 10% HCl is added to correct the pH. It is stirred 0.25 hours and the phases are separated. The aqueous phase is again extracted with 250 ml (5 V) of Toluene. The organic phases, which are washed with 250 ml (5 V) of a saturated sodium chloride solution, are recombined. The phases are separated and the organic solution is sampled for HPLC checking. The organic phase is extracted with a soda solution 1 M (the product passes into aqueous phase), prepared by mixing 25 ml (0.5 V) of caustic soda solution 30% and 225 ml (4.5 V) of purified water. Before performing separation, check the pH which must be greater than 10. There is separation of the organic phase which is again re-extracted with caustic soda solution 1 M, prepared by mixing 25 ml (0.5 V) of caustic soda solution 30% and 225 ml (4.5 V) of purified water. Before performing separation, the pH, which must be greater than 10, is checked. There is separation of the organic phase which is again re-extracted with 1 M caustic soda solution, prepared by mixing 25 ml (0.5 V) of caustic soda solution 30% and 225 ml (4.5 V) of purified water. Before performing separation, the pH, which must be greater than 10, is checked. The aqueous phases which are washed with 2×100 ml (2×2 V) of ethyl acetate are recombined. The organic phase is discarded. The pH of the aqueous phase (containing the reaction product) is corrected with hydrochloric acid to a final pH of 6-7. The aqueous phase is extracted with 2×250 ml (2×5 V) of Ethyl acetate. The product passes into the organic phase. The organic phases are recombined and washed with 250 ml (5 V) of saturated solution of sodium chloride. The phases are separated and the organic solution is sampled for HPLC checking. There are added to the organic phase 23 g=21.8 ml (1.1 equiv.) of 1,3-propanediol (d=1.0597 g/ml). It is stirred at 20-25° C. for 2 h and the conversion in checked in TLC. If the reaction is complete, the aqueous phase is separated (water is generated during the reaction) and is concentrated to residue at $T_{bath}$ 35-40° C. It is taken up with 250 ml (5 V) of Dichloromethane and the organic phase is washed with 50 ml (1.0 V) of purified water. It is concentrated to residue in $T_{bath}$ 35-40° C. 150 ml (3.0 V) of n-Hexane are slowly added under agitation. The product crystallizes. It is stirred at 20-25° C. for 0.5 h and then at 0-5° C. for 0.5 h. It is filtered by washing with 50 ml (1.0 V) of n-Hexane pre-cooled to 0-5° C. It is vacuum dried at 20-25° C. for at least 8 h. There are obtained 23.0 g of 2-(1,3,2-dioxaborinane-2-yl)benzonitrile equal to a molar yield from 2-bromo benzonitrile of 44.8%. HPLC purity (A/A % 99.7%.).

Example 2

Synthesis of 2-(1,3,2-dioxaborinane-2-yl)benzonitrile—Effect of the Temperature in Step a) on Molar Yield and Chemical Purity Synthesis Pathway

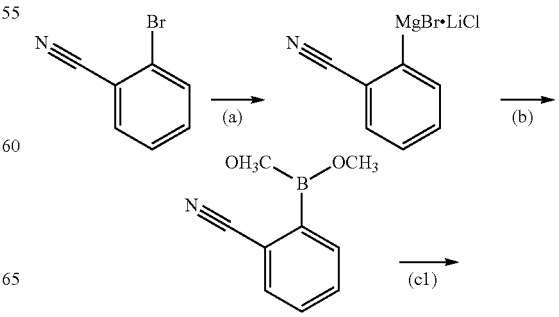

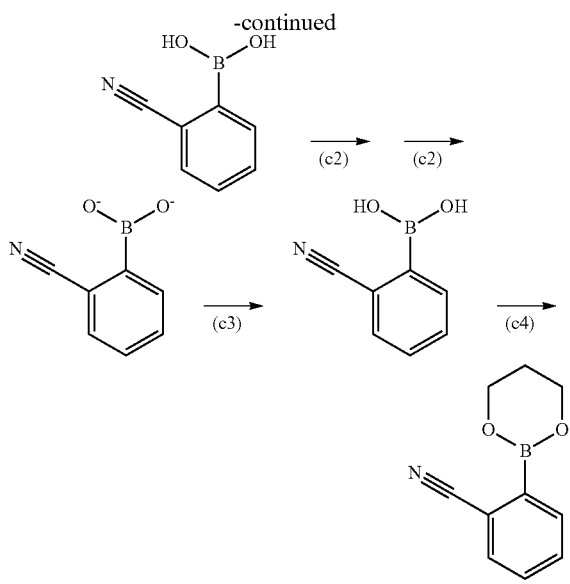

Into a previously dried flask, equipped with a thermometer, condenser and dropping funnel, under nitrogen flow, 100.0 g (1.00 equiv.) of 2-bromobenzonitrile and 750 ml (7.5 V) of anhydrous Toluene are charged. The mixture is cooled at −22/−18° C. and 519.0 g (1.30 equiv.) of Isopropylmagnesium chloride/lithium chloride complex 1.3 M (about 20% wt/wt) in THF are added keeping the T at −22/−18° C., over about 1.5 h. The reaction is stirred at −22/−18° C. for additional 4 h then the conversion in checked by HPLC. When the reaction is complete, 125.6 g (2.20 equiv.) of trimethylborate are added keeping the T at −22/−18° C. over about 0.5 h. Once the addition is complete, cooling is removed and the reaction is warmed to 20-25° C. and stirred for about 0.5 h. The conversion is checked by HPLC. When the reaction is complete, the mixture is cooled to 0-5° C. and a solution of 0.1 M hydrochloric acid, prepared by mixing 10 ml of 32% hydrochloric acid (10.17 M) and 990 ml (9.9 V) of purified water, is added at 0-20° C. After stirring 0.25 h at 20-25° C. the pH is modified to 3-4 with appropriate amount of 32% hydrochloric acid. The layers are then separated. The aqueous phase is extracted again with 500 ml (5 V) of Toluene. The organic phases are recombined and washed with 500 ml (5 V) of a saturated sodium chloride solution. The organic layer is extracted at 20-25° C. with 0.1 M sodium hydroxide solution, prepared by mixing 5 ml (0.05 V) of 30% sodium hydroxide solution and 495 ml (4.95 V) of purified water (the product passes into the aqueous phase). Before performing layer separation the pH is modified to 10-11 with the appropriate amount of 30% sodium hydroxide solution. Layers are separated and the organic layer is extracted twice with 0.1 M sodium hydroxide solution, prepared by mixing 5 ml (0.05 V) of 30% sodium hydroxide solution and 495 ml (4.95 V) of purified water. The pH is corrected to 10-11 if needed before each layer separation. The aqueous phases are recombined and are washed with 2×300 ml (2×3 V) of Isopropyl acetate. The organic phase is discarded. The pH of the aqueous phase (containing the reaction product) is corrected with hydrochloric acid to a final pH of 3-4. The aqueous phase is extracted with 2×500 ml (2×5 V) of Isopropyl acetate. The product passes into the organic phase. 46.0 g (1.1 equiv.) of 1,3-propanediol are then added to the organic solution and the mixture stirred at 20-25° C. for 2 h. The conversion in checked by TLC. When the reaction is complete, the aqueous phase is separated (water is generated during the reaction) and the organic layer is concentrated to residue at T bath 35-40° C. The residue is dissolved with 500 ml (5 V) of Dichloromethane and the organic phase is washed with 100 ml (1.0 V) of purified water. Layers are separated and the organic phase is concentrated to small volume in T bath 35-40° C. 100 ml (1.0 V) of n-Heptane are added keeping boiling under vacuum at T bath 35-40° C. and the mixture is concentrated to small volume. Then, 5 ml of Isopropanol and 300 ml (3.0 V) of n-Heptane are slowly added under vigorous stirring. The product crystallizes out. The slurry is stirred at 20-25° C. for 0.5 h and then at 0-5° C. for at least 2 h. The mixture is filtered and washed with 100 ml (1.0 V) of n-Heptane pre-cooled to 0-5° C. After vacuum drying at 20-25° C. for at least 8 h 75.1 g of 2-(1,3,2-dioxaborinane-2-yl)benzonitrile equal to a molar yield from 2-bromo benzonitrile of 73%. HPLC purity (A/A % 99.9%).

In particular, it will be appreciable how the employing of the conditions object of the present invention allow the 2-cyanophenylboronic acid of formula (I) or an ester thereof to be obtained with good yields, high purity, in a single step and avoiding the use of cryogenic conditions and equipment.

The invention claimed is:

1. Process for the preparation of an ester of 2-cyanophenylboronic acid of formula (II):

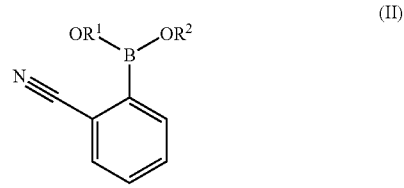

wherein $R^1$ and $R^2$ are independently linear or branched $C_1$-$C_6$ alkyl groups or are joined to form a cycle containing between 1 and 6 possibly substituted carbon atoms, comprising:

(a) converting a 2-halogenbenzonitrile of formula (IV):

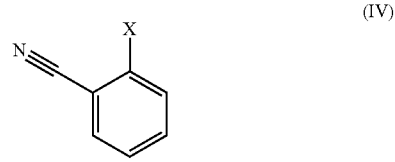

wherein X is selected from the group consisting of chlorine, bromide and iodine, in a 2-cyanophenyl magnesium halide lithium chloride complex of formula (III):

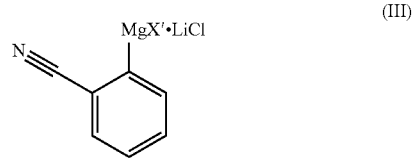

wherein X' is selected from the group consisting of chlorine, bromine and iodine; and (b) converting the compound obtained in step (a) to give the compound of formula (II).

2. Process according to claim 1, comprising the further conversion step (c1) of the compound obtained in step (b) in the 2-cyanophenylboronic acid of formula (I):

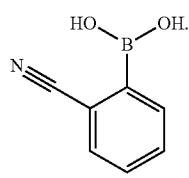

3. Process according to claim 2, comprising the further conversion step (c2) of the compound obtained in step (c1) in an organic or inorganic salt of the 2-cyanophenylboronic acid of formula (I).

4. Process according to claim 1, comprising the further direct conversion step (c6) of the compound obtained in step (b) in an organic or inorganic salt of the 2-cyanophenylboronic acid of formula (I).

5. Process according to claim 3, comprising the further conversion step (c3) of the compound obtained in steps (c2) or (c6) in the 2-cyanophenylboronic acid of formula (I).

6. Process according to claim 5, comprising the further conversion step (c4) of the compound obtained in step (c3) in an ester of the 2-cyanophenylboronic acid of formula (V):

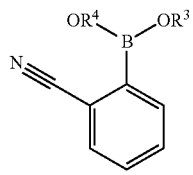

wherein $R^3$ and $R^4$ are independently linear or branched $C_1$-$C_6$ alkyl groups or are joined to form a cycle containing between 1 and 6 possibly substituted carbon atoms.

7. Process according to claim 3, comprising the further conversion step (c8) of the compound obtained in step (c2) in an ester of the 2-cyanophenylboronic acid of formula (V):

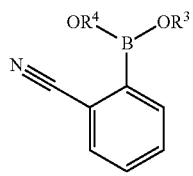

wherein $R^3$ and $R^4$ are independently $C_1$-$C_6$ linear or branched alkyl groups or are joined to form a cycle containing between 1 and 6 possibly substituted carbon atoms.

8. Process according to claim 1, wherein the prepared compound is the 2-(1,3,2-dioxaborinane-2-yl)benzonitrile of the following formula:

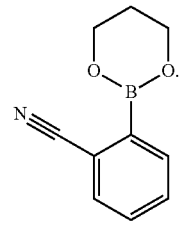 [SMILES: N#Cc1ccccc1B1OCCCO1]

9. Process according to claim 1, wherein step (a) X is bromine.

10. Process according to claim 1, wherein the step (a) is performed by means of a Lithium chloride complex Grignard reagent.

11. Process according to claim 10, wherein the Grignard reagent is selected from the group consisting of Isopropylmagnesium chloride lithium chloride complex and t-Butylmagnesium chloride lithium chloride complex.

12. Process according to claim 1, wherein the step (a) is performed at a temperature between −25° C. and −15° C.

13. Process according to claim 1, wherein step (b) is performed by means of a compound of formula X1-B(OR1)(OR2) where X1 is selected from the group consisting of halogen and OR wherein R is a linear or branched $C_1$-$C_6$ alkyl group and where $R^1$ and $R^2$ are independently linear or branched $C_1$-$C_6$ alkyl groups or are joined to form a cycle containing between 1 and 6 possibly substituted carbon atoms.

14. Process according to claim 13, wherein X1 is selected from the group consisting of chlorine, OMe and OiPr and $R^1$ and $R^2$ are selected from Methyl, isopropyl or form a cycle containing 3 unsubstituted carbon atoms.

15. Process according to claim 3, wherein step (c2) is performed by means of the extraction of an organic solution of the compound of formula (I) with an aqueous solution at pH greater than 9 comprising an organic or inorganic base, wherein the organic or inorganic salt of the 2-cyanophenylboronic acid of formula (I) thus generated is then to be found.

16. Process according to claim 15, wherein the pH of the aqueous solution is between 10 and 14.

17. Process according to claim 1, wherein steps (a) and/or (b) are performed in Toluene or a mixture of Toluene and THF.

18. Process according to claim 1 wherein the step a) is carried out within a range of temperature between −25° C. and −15° C. and the process comprises the conversion step (c1) of the compound obtained in step (b) in the 2-cyanophenylboronic acid of formula (I):

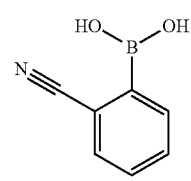

and comprises the conversion step (c2) of the compound obtained in step (c1) in an organic or inorganic salt of the 2-cyanophenylboronic acid of formula (I), or, alternatively to the steps (c1) and (c2), the process comprises the direct conversion step (c6) of the compound obtained in step (b) in an organic or inorganic salt of the 2-cyanophenylboronic acid of formula (I) which is then converted in the ester of 2-cyanophenylboronic acid of formula (V):

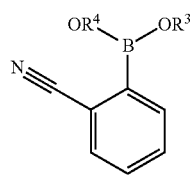

(V)

wherein $R^3$ and $R^4$ are independently $C_1$-$C_6$ linear or branched alkyl groups or are joined to form a cycle containing between 1 and 6 possibly substituted carbon atoms, through the step (c8) or the steps (c3) and (c4).

19. Process for the preparation of 2-Cyanophenylboronic acid of formula (I) or a salt thereof:

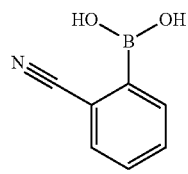

(I)

comprising the extraction of an organic solution of the compound of formula (I) with an aqueous solution at pH greater than 9 comprising an organic or inorganic base, wherein the organic or inorganic salt of 2-cyanophenylboronic acid of formula (I) thus generated is then to be found.

20. Organic or inorganic salt of the cyanophenylboronic acid of formula (I):

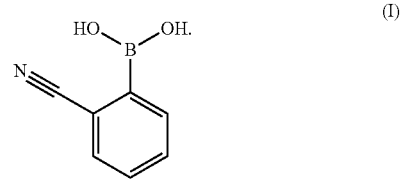

(I)

21. A salt according to claim 20, wherein said salt is selected from the group consisting of sodium salt, potassium salt and magnesium salt.

* * * * *